US00PP19034P2

(12) United States Plant Patent
Leue

(10) Patent No.: US PP19,034 P2
(45) Date of Patent: Jul. 15, 2008

(54) *ANGELONIA* PLANT NAMED 'BALANGSPRI'

(50) Latin Name: *Angelonia angustifolia*
Varietal Denomination: Balangspri

(75) Inventor: Ellen Leue, DeKalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/823,388

(22) Filed: Jun. 27, 2007

(51) Int. Cl.
*A01H 5/00* (2006.01)

(52) U.S. Cl. ..... Plt./404

(58) Field of Classification Search ..... Plt./404
See application file for complete search history.

(56) References Cited

U.S. PATENT DOCUMENTS

PP16,555 P2 * 5/2006 Leue ..... Plt./404

* cited by examiner

*Primary Examiner*—Wendy C. Haas
(74) *Attorney, Agent, or Firm*—Audrey Charles

(57) ABSTRACT

A new and distinct cultivar of *Angelonia* plant named 'Balangspri', characterized by its white-colored flowers, medium green-colored foliage, and moderately vigorous, compact, and prostrate growth habit.

1 Drawing Sheet

Latin name of genus and species of plant claimed: *Angelonia angustifolia.*
Variety denomination: 'Balangspri'.

BACKGROUND OF THE INVENTION

The present invention relates to a new and distinct cultivar of *Angelonia* plant botanically known as *Angelonia angustifolia* and hereinafter referred to by the cultivar name 'Balangspri'.

The new cultivar originated in a controlled breeding program in Elburn, Ill. during May 2003. The objective of the breeding program was the development of *Angelonia* cultivars with unique flower coloration, continuous flowering, and a moderately vigorous, freely branching, and upright to prostrate growth habit.

The new *Angelonia* cultivar is the result of cross-pollination. The female (seed) parent of the new cultivar is the proprietary *Angelonia angustifolia* breeding selection designated 147-1,2-6-2-3, not patented, characterized by its white-colored flowers, medium-dark green-colored foliage, and semi-prostrate growth habit. The male (pollen) parent of the new cultivar is the proprietary *Angelonia angustifolia* breeding selection designated 202-1, not patented, characterized by its dark violet-colored flowers, dark green-colored foliage, and semi-prostrate growth habit. The new cultivar was discovered and selected as a single flowering plant within the progeny of the above stated cross-pollination during March 2004 in a controlled environment at Elburn, Ill.

Asexual reproduction of the new cultivar by terminal stem cuttings since March 2004 at Elburn, Ill. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balangspri' as a new and distinct cultivar of *Angelonia* plant:

1. White-colored flowers;
2. Medium green-colored foliage; and
3. Moderately vigorous, compact, and prostrate growth habit.

Plants of the new cultivar differ from plants of the female parent primarily in growth habit and from plants of the male parent primarily in flower color, flower size, and leaf size. Plants of the new cultivar have smaller leaves and smaller flowers than plants of the male parent.

Of the many commercially available *Angelonia* cultivars known to the inventor, the most similar in comparison to the new cultivar is AngelMist® Basket White 'Balangbawi', U.S. Plant Pat. No. 16,555. However, in side by side comparisons, plants of the new cultivar differ from plants of 'Balangbawi' in the following characteristics:

1. Plants of the new cultivar have more inflorescences than plants of 'Balangbawi'; and
2. Plants of the new cultivar are more compact, as measured by plant width, than plants of 'Balangbawi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balangspri'. The plants were grown in 4.5 inch pots for 6 weeks in a greenhouse at West Chicago, Ill. Plants were given one pinch at transplant.

DETAILED BOTANICAL DESCRIPTION

Figure 1:
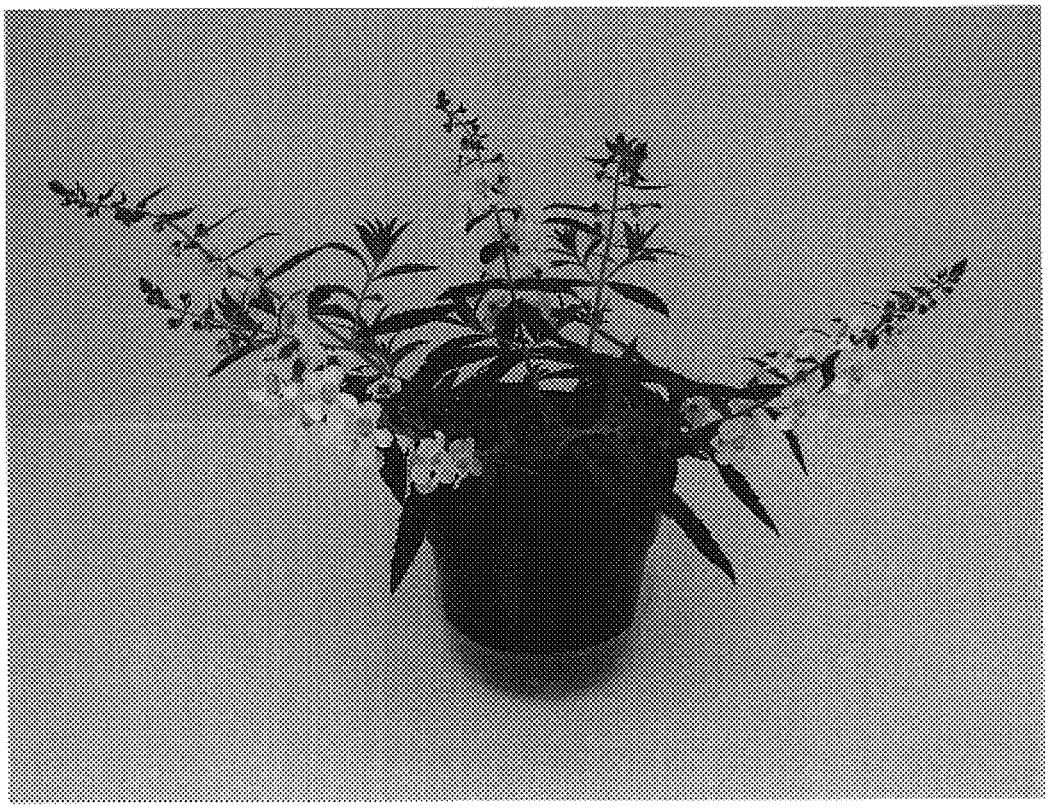
FIG. 1 illustrates a side view of the overall growth and flowering habit of 'Balangspri'.
Figure 2:
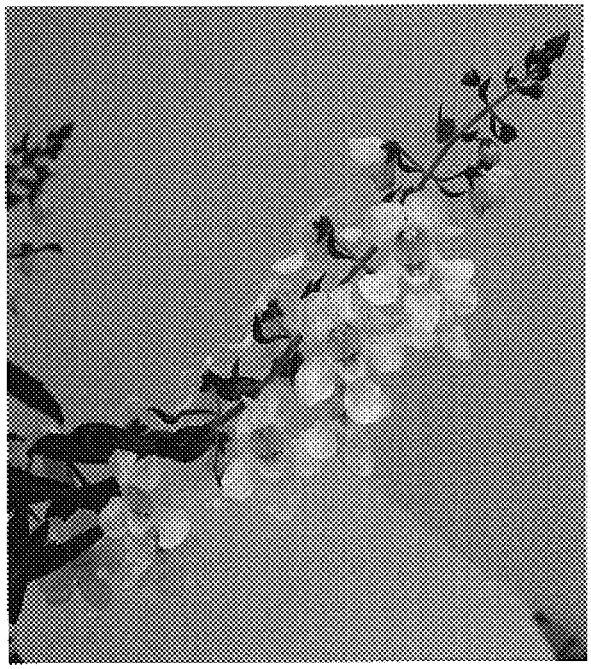
FIG. 2 illustrates a close-up view of an individual inflorescence of 'Balangspri'.
Figure 3:
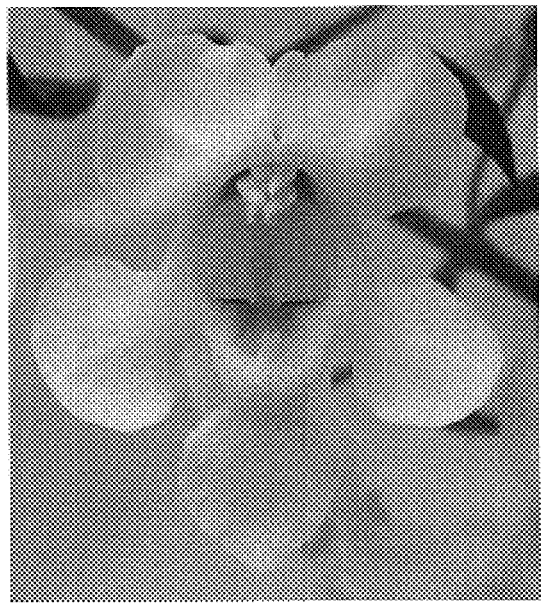
FIG. 3 illustrates a close-up view of an individual flower of 'Balangspri'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 1, 2007 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 6 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Angelonia angustifolia* cultivar Balangspri.

Parentage:

*Female parent.*—Proprietary *Angelonia angustifolia* breeding selection designated 147-1,2-6-2-3, not patented.

*Male parent.*—Proprietary *Angelonia angustifolia* breeding selection designated 202-1, not patented.

Propagation:

*Type cutting.*—Terminal stem.

*Time to initiate roots.*—Approximately 7 to 9 days.

*Time to produce a rooted cutting.*—Approximately 24 to 28 days.

*Root description.*—Fine, fibrous.

*Rooting habit.*—Freely branching.

Plant description:

*Commercial crop time.*—Approximately 5 to 8 weeks from a rooted cutting to finish in an 11 cm to 13 cm pot.

*Growth habit and general appearance.*—Moderately vigorous, compact, prostrate.

*Size.*—Height from soil level to top of plant plane: Approximately 15.3 cm. Width: Approximately 32.6 cm.

*Branching habit.*—Freely branching, pinching enhances basal branching. Plants become densely branched with age. Quantity of main branches per plant: Approximately 4.

*Branch.*—Shape: Square in cross section. Strength: Strong. Length to base of raceme: Approximately 7.9 cm. Diameter: Approximately 3.0 mm. Length of central internode: Approximately 1.7 cm. Texture: Densely glandular pubescent. Gland color: Colorless, transparent. Color of young and mature stems: 144B.

Foliage description:

*General description.*—Quantity of leaves per main branch: Approximately 16. Fragrance: Slight. Form: Simple. Arrangement: Opposite.

*Leaves.*—Aspect: Perpendicular or obtuse angle to stem. Shape: Elliptic. Margin: Widely serrate. Apex: Acute. Base: Sessile. Venation pattern: Pinnate. Length of mature leaf: Approximately 5.5 cm. Width of mature leaf: Approximately 1.0 cm. Texture of upper and lower surfaces: Sparsely glandular pubescent. Gland color: Colorless, transparent. Color of upper surface of young foliage: 137C with venation of 144B. Color of lower surface of young foliage: 138B with venation of 138D. Color of upper surface of mature foliage: 137A with venation of 144B. Color of lower surface of mature foliage: 138A with venation of 138D.

Flowering description:

*Flowering habit.*—'Balangspri' is freely flowering under outdoor growing conditions with substantially continuous blooming from spring through autumn and year-round in greenhouse environment.

*Lastingness of individual flower on the plant.*—Approximately 7 to 10 days.

Inflorescence description:

*General description.*—Type: Terminal raceme. Quantity per plant: Approximately 4. Fragrance: Slight, sweet. Length or height: Approximately 15.2 cm. Width: Approximately 4.3 cm. Quantity of fully open flowers per inflorescence: Approximately 16.

Flower description:

*Type.*—Solitary, zygomorphic.

*Bud.*—Rate of opening: Generally takes 3 to 4 days for bud to progress from first color to fully open flower.

*Bud just before opening.*—Shape: Globular. Length: Approximately 6.8 mm. Diameter: Approximately 6.8 mm. Color of upper surface: 1D. Color of lower surface: 145B.

*Corolla.*—Shape: Bilabiate. Aspect: Facing outward. Length: Approximately 2.3 cm. Width: Approximately 2.1 cm. Depth: Approximately 6.3 mm.

*Petals.*—Quantity: 5, fused at base forming a throat and consisting of an upper lip with 2 petals and a lower lip with 3 petals, 2 lateral petals and one central petal. Shape: Obovate. Margin: Entire. Apex: Obtuse.

*Upper lip.*—Length of petals from throat: Approximately 7.0 mm. Width of each petal: Approximately 1.0 cm. Texture of upper and lower surfaces: Sparsely glandular pubescent. Gland color: Colorless, transparent. Color of upper and lower surfaces when fully open: Purer white than 155D.

*Lower lip, lateral petals.*—Length of petals from throat: Approximately 8.0 mm. Width of each petal: Approximately 8.3 mm. Texture of upper surface: Sparsely glandular pubescent. Gland color: Colorless, transparent and at base 144D, transparent. Texture of lower surface: Densely glandular pubescent. Gland color: Colorless, transparent with base of 144D, transparent. Color of upper and lower surfaces when fully open: Purer white than 155D.

*Lower lip, central petal.*—Length from the palate: Approximately 8.6 mm. Width: Approximately 6.9 mm. Texture of upper surface: Sparsely glandular pubescent. Gland color: Colorless, transparent and at base 144D, transparent. Texture of lower surface: Densely glandular pubescent. Gland color: Colorless, transparent with base of 144D, transparent. Color of upper and lower surfaces when fully open: Purer white than 155D.

*Throat.*—Length: Approximately 7.7 mm. Width: Approximately 5.7 mm. Texture of inner surface:

Glabrous with two densely glandular pubescent areas behind palate. Gland color: 143B, transparent. Texture of outer surface: Glabrous. Color of inner surface: Purer white than 155D with two areas behind palate of 143A and an overlay of 143A at anthers. Color of outer surface: 155C. Palate color: N144C. Palate texture: Glabrous. Teeth color: Purer white than 155D with an overlay of N144D at tips.

*Calyx.*—Shape: Star, cupped. Diameter: Approximately 6.0 mm.

*Sepals.*—Quantity per flower: 5. Shape: Lanceolate. Apex: Acute. Base: Fused. Length: Approximately 4.0 mm. Width: Approximately 2.0 mm. Texture of upper surface: Sparsely glandular pubescent. Gland color: Colorless, transparent. Texture of lower surface: Sparsely glandular pubescent. Gland color: 144D. Color of upper surface: 144A. Color of lower surface: 143A at base and center with 144A at apex.

*Pedicel.*—Strength: Strong, flexible. Aspect: Acute angle to stem. Length: Approximately 1.0 cm. Diameter: Approximately 1.0 mm. Texture: Sparsely glandular pubescent. Gland color: 144D, transparent. Color: 144B.

*Reproductive organs.*—Androecium: Stamen quantity: 4 per flower. Filament length: Approximately 4.0 mm. Filament color: Purer white than 155D, opaque. Anther shape: Bilobed. Anther length: Approximately 1.0 mm. Anther color: 155D. Pollen amount: Moderate. Pollen color: 155D. Gynoecium: Pistil quantity: 1 per flower. Pistil length: Approximately 4.0 mm. Stigma shape: Pointed. Stigma length: Less than 1 mm. Stigma color: Colorless, opaque. Style length: Approximately 3.0 mm. Style color: Purer white than 155D. Ovary diameter: Approximately 1.0 mm. Ovary texture: Densely glandular pubescent. Gland color: 144D. Ovary color: 149C.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balangspri', substantially as herein shown and described.

* * * * *